(12) United States Patent
Cao et al.

(10) Patent No.: US 10,576,288 B2
(45) Date of Patent: Mar. 3, 2020

(54) CARDIAC EVENT SENSING IN AN IMPLANTABLE MEDICAL DEVICE

(71) Applicant: Medtronic, Inc., Minneapolis, MN (US)

(72) Inventors: Jian Cao, Shoreview, MN (US); Alan Cheng, Golden Valley, MN (US)

(73) Assignee: Medtronic, Inc., Minneapolis, MN (US)

(*) Notice: Subject to any disclaimer, the term of this patent is extended or adjusted under 35 U.S.C. 154(b) by 296 days.

(21) Appl. No.: 15/497,546

(22) Filed: Apr. 26, 2017

(65) Prior Publication Data

US 2018/0311504 A1     Nov. 1, 2018

(51) Int. Cl.

| *A61N 1/365* | (2006.01) |
|---|---|
| *A61B 5/04* | (2006.01) |
| *A61B 5/0464* | (2006.01) |
| *A61N 1/39* | (2006.01) |
| *A61N 1/372* | (2006.01) |

(52) U.S. Cl.
CPC ..... *A61N 1/36592* (2013.01); *A61N 1/37217* (2013.01); *A61N 1/37247* (2013.01); *A61N 1/3987* (2013.01); *A61B 5/04012* (2013.01); *A61B 5/0464* (2013.01)

(58) Field of Classification Search
CPC ............ A61N 1/36592; A61N 1/39622; A61N 1/3704; A61N 1/365; A61N 1/37247; A61N 1/37217; A61N 1/3987; A61N 1/0563; A61N 1/0504; A61B 5/0452; A61B 5/042; A61B 5/6869; A61B 5/4836; A61B 5/0468; A61B 5/04525; A61B 5/7282; A61B 5/0464; A61B 5/04012
See application file for complete search history.

(56) References Cited

U.S. PATENT DOCUMENTS

| 7,761,150 | B2 | 7/2010 | Ghanem et al. |
|---|---|---|---|
| 8,583,221 | B1 | 11/2013 | Patel et al. |
| 8,694,097 | B2 | 4/2014 | Cao et al. |
| 8,781,585 | B2 | 7/2014 | Gunderson et al. |
| 9,339,662 | B2 | 5/2016 | Allavatam et al. |
| 9,468,766 | B2 | 10/2016 | Sheldon et al. |
| 2015/0306375 | A1 | 10/2015 | Marshall et al. |
| 2015/0306410 | A1 | 10/2015 | Marshall et al. |
| 2016/0106989 | A1 | 4/2016 | Stadler et al. |
| 2016/0144190 | A1 | 5/2016 | Cao et al. |
| 2016/0158567 | A1 | 6/2016 | Marshall et al. |

(Continued)

OTHER PUBLICATIONS (PCT/US2018/027704) PCT Notification of Transmittal of the International Search Report and the Written Opinion of the International Searching Authority, dated Jul. 16, 2018, 13 pages.

(Continued)

*Primary Examiner* — Mark Bockelman

(57) ABSTRACT

An implantable medical device performs a method that includes detecting a cardiac event interval that is greater than a P-wave oversensing threshold interval. In response to detecting the cardiac event interval greater than the P-wave oversensing threshold interval, the device determines the amplitude of the sensed cardiac signal and withholds restarting a pacing interval in response to the amplitude satisfying P-wave oversensing criteria. A pacing pulse may be generated in response to the pacing interval expiring without sensing an intrinsic cardiac electrical event that is not detected as a P-wave oversensing event.

20 Claims, 10 Drawing Sheets

(56) References Cited

U.S. PATENT DOCUMENTS

2017/0312532 A1    11/2017   Zhang et al.
2017/0354827 A1    12/2017   Zhang

OTHER PUBLICATIONS

Cao et al., "Multi-Threshold Sensing of Cardiac Electrical Signals in an Extracardiovascular Implantable Cardioverter Defibrillator", U.S. Appl. No. 15/142,171, filed Apr. 29, 2016, 71 pages.

CARDIAC EVENT SENSING IN AN IMPLANTABLE MEDICAL DEVICE

TECHNICAL FIELD

The disclosure relates generally to implantable medical devices (IMDs) and methods for sensing cardiac electrical events from a cardiac electrical signal and in particular to methods for detecting oversensing of atrial P-waves attendant to atrial depolarizations.

BACKGROUND

Medical devices, such as cardiac pacemakers and implantable cardioverter defibrillators (ICDs), provide therapeutic electrical stimulation to a heart of a patient via electrodes carried by one or more medical electrical leads and/or electrodes on a housing of the medical device. The electrical stimulation may include cardiac pacing pulses and/or cardioversion/defibrillation (CV/DF) shocks.

The medical device may sense cardiac electrical events attendant to the intrinsic heart activity for detecting an abnormal intrinsic heart rhythm. Upon detection of an abnormal rhythm, such as bradycardia, tachycardia or fibrillation, an appropriate electrical stimulation therapy may be delivered to restore or maintain a more normal rhythm of the heart. For example, an ICD may deliver pacing pulses to the heart of the patient upon detecting bradycardia or tachycardia or deliver CV/DF shocks to the heart upon detecting tachycardia or fibrillation.

The ICD may sense the cardiac electrical signals from a heart chamber and deliver electrical stimulation therapies to the heart chamber using endocardial electrodes carried by transvenous medical electrical leads. In other cases, a non-transvenous lead may be coupled to the ICD, in which case the ICD may sense cardiac electrical signals and deliver electrical stimulation therapy to the heart using extra-cardiovascular electrodes. Cardiac event signals, such as atrial P-waves and ventricular R-waves, sensed by electrodes positioned within the atrial or ventricular heart chamber from which the signal arises, generally have a high signal strength for reliably sensing the cardiac electrical events. In other examples, a non-transvenous lead may be coupled to the ICD, carrying electrodes positioned at extra-cardiovascular locations, in which case the cardiac event amplitudes may have a relatively lower or more variable signal strength and/or different relative amplitudes between R-waves, T-waves and P-waves in the cardiac electrical signal. Reliable sensing of cardiac events by a pacemaker of ICD is important in determining when an electrical stimulation therapy is needed and delivering the appropriate electrical stimulation therapy for treating an abnormal heart rhythm.

SUMMARY

In general, the disclosure is directed to techniques for sensing cardiac event signals from a cardiac electrical signal and in particular for identifying P-wave oversensing. An IMD operating according to the techniques disclosed herein is configured to sense cardiac events, identify oversensed P-wave events, and neglect sensed events identified as oversensed P-waves in inhibiting pacing pulses and controlling a ventricular pacing interval and/or in determining a ventricular rate for detecting ventricular tachyarrhythmias. The IMD may operate to detect P-wave oversensing (PWOS) by a comparative analysis of the maximum peak amplitudes of two different cardiac electrical signals received by the IMD.

In one example, the disclosure provides an IMD including a therapy delivery circuit configured to generate cardiac pacing pulses, a sensing circuit configured to receive a cardiac signal from a patient's heart via sensing electrodes and sense intrinsic cardiac electrical events from the cardiac signal, and a control circuit coupled to the sensing circuit and the therapy delivery circuit. The control circuit is configured to start a pacing interval and detect an event interval that is greater than a P-wave oversensing threshold interval. The event interval is determined as the time interval extending from an intrinsic cardiac electrical event sensed by the sensing circuit from the cardiac signal to a most recent preceding cardiac event. The control circuit determines an amplitude of the cardiac signal in response to detecting the event interval greater than the P-wave oversensing threshold interval, withholds restarting of the pacing interval in response to at least the amplitude satisfying P-wave oversensing criteria, and controls the therapy delivery circuit to generate a pacing pulse in response to the pacing interval expiring.

In another example, the disclosure provides a method including sensing intrinsic cardiac electrical events from a cardiac signal received by a sensing circuit of an implantable medical device from a patient's heart via sensing electrodes, starting a pacing interval by a control circuit of the implantable medical device and detecting an event interval that is greater than a P-wave oversensing threshold interval. The event interval extends from an intrinsic cardiac electrical event sensed from the cardiac signal by the sensing circuit to a most recent preceding cardiac event. The method further includes determining an amplitude of the cardiac signal in response to detecting the event interval greater than the P-wave oversensing threshold interval and withholding restarting of the pacing interval in response to at least the amplitude satisfying P-wave oversensing criteria. The method includes generating a pacing pulse by a therapy delivery circuit of the implantable medical device in response to the pacing interval expiring.

In another example, the disclosure provides a non-transitory, computer-readable storage medium storing a set of instructions which, when executed by a control circuit of an IMD, cause the IMD to sense intrinsic cardiac electrical events from a cardiac signal, start a pacing interval, detect an event interval that is greater than a P-wave oversensing threshold interval where the event interval extends from an intrinsic cardiac electrical event sensed from the cardiac signal to a most recent preceding cardiac event. The IMD is further caused to determine an amplitude of the cardiac signal in response to detecting the event interval greater than the P-wave oversensing threshold interval, withhold restarting of the pacing interval in response to the amplitude satisfying P-wave oversensing criteria, and generate a pacing pulse in response to the pacing interval expiring.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for detecting P-wave oversensing by a cardiac medical device or system. A cardiac medical device may be configured to sense R-waves attendant to ventricular depolarizations for use in controlling ventricular pacing. A ventricular pacing interval may be started in response to sensing an intrinsic R-wave and if the pacing interval expires before another R-wave is sensed, a pacing pulse is delivered. In some instances, atrial P-waves attendant to atrial depolarizations may be oversensed as R-waves. An oversensed P-wave may cause the cardiac medical device to inhibit a ventricular pacing pulse when the pacing pulse is actually needed to maintain the ventricular rate at a programmed lower pacing rate. By identifying a sensed cardiac event as an oversensed P-wave, P-waves falsely sensed as R-waves may be neglected in inhibiting pacing pulses and controlling a ventricular pacing interval and/or in determining a ventricular rate for detecting ventricular tachyarrhythmias.

In some examples, the cardiac medical device system may be an extra-cardiovascular ICD system. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The techniques disclosed herein for detecting P-wave oversensing may be applied to a cardiac electrical signal acquired using extra-cardiovascular electrodes.

These P-wave oversensing techniques are described herein in conjunction with an ICD and implantable medical lead carrying extra-cardiovascular electrodes, but aspects disclosed herein may be utilized in conjunction with other cardiac medical devices or systems. For example, the techniques for detecting P-wave oversensing as described in conjunction with the accompanying drawings may be implemented in any implantable or external medical device enabled for sensing intrinsic cardiac electrical events from cardiac signals received from a patient's heart via sensing electrodes, including implantable pacemakers, ICDs or cardiac monitors coupled to transvenous, pericardial or epicardial leads carrying sensing and therapy delivery electrodes; leadless pacemakers, ICDs or cardiac monitors having housing-based sensing electrodes; and external or wearable pacemakers, defibrillators, or cardiac monitors coupled to external, surface or skin electrodes.

Figure 1A:
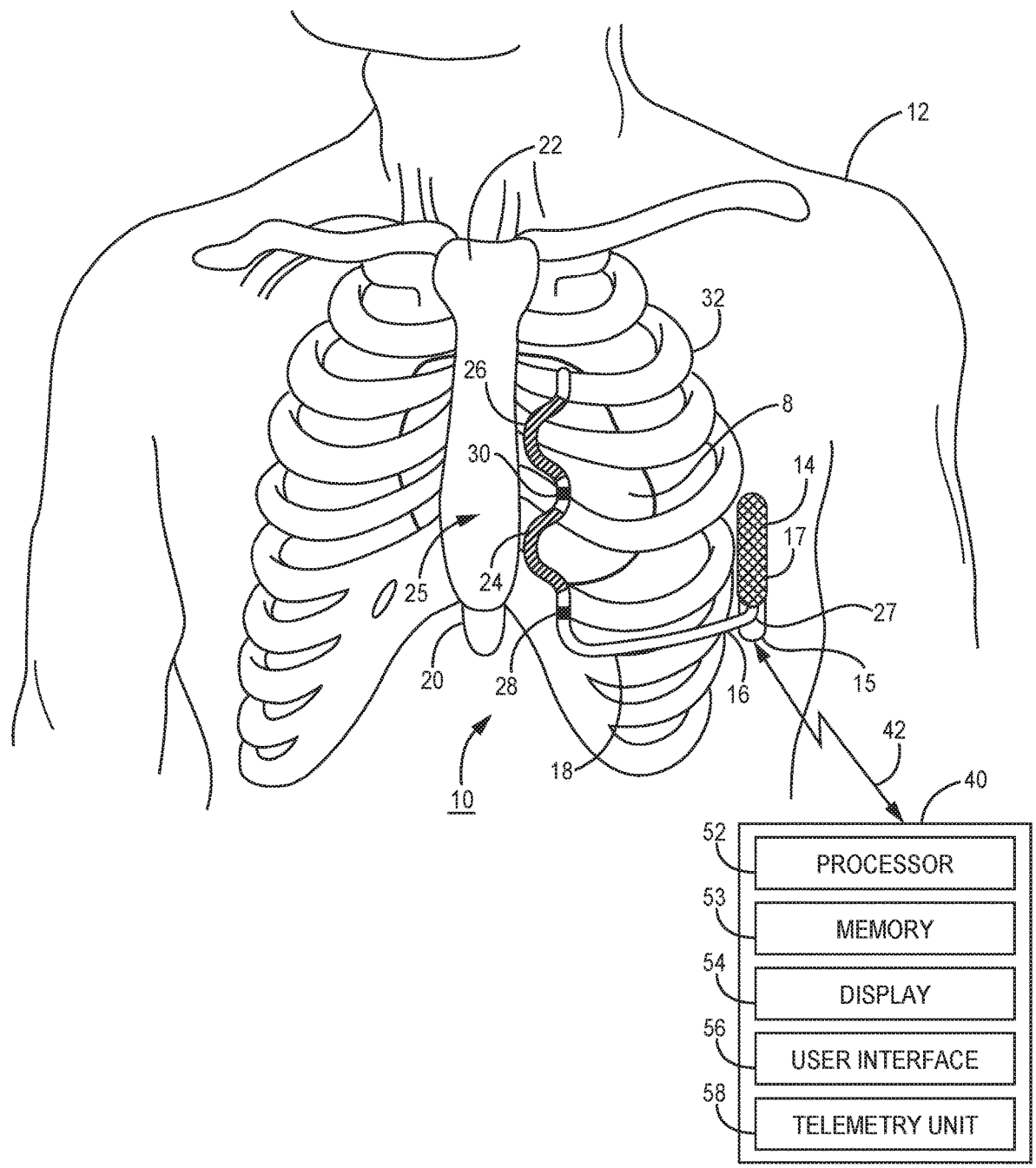
FIGS. 1A and 1B are conceptual diagrams of an extra-cardiovascular ICD system according to one example.
Figure 1B:
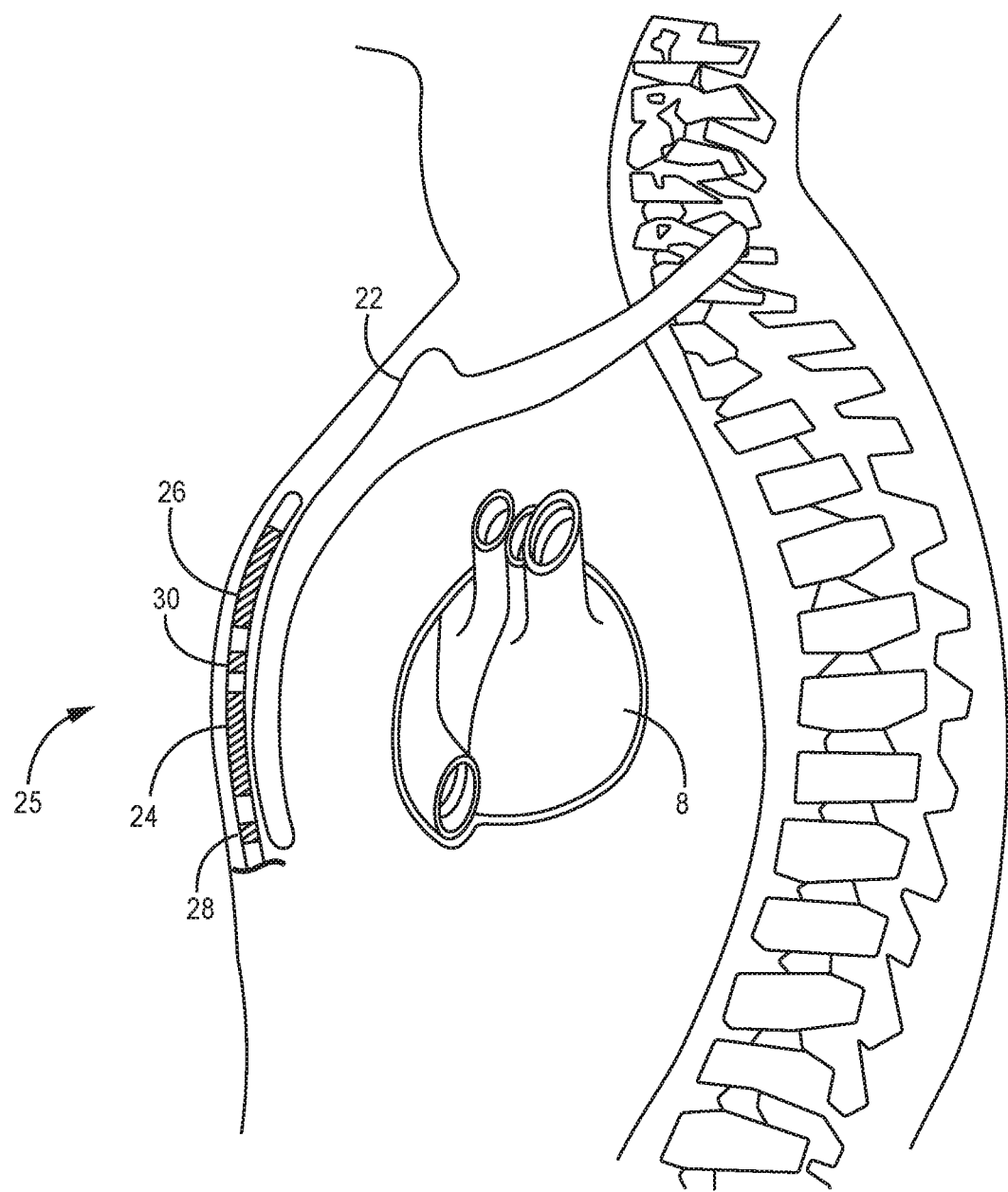

FIGS. 1A and 1B are conceptual diagrams of an extra-cardiovascular ICD system 10 according to one example.

FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, electrical cardiac signal sensing circuitry, therapy delivery circuitry, power sources and other components for sensing cardiac electrical signals, detecting a heart rhythm, and controlling and delivering electrical stimulation pulses to treat an abnormal heart rhythm.

Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, electrodes 24 and 26 may be used as sensing electrodes in a sensing vector for sensing cardiac electrical signals and determining a need for an electrical stimulation therapy.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., used as either a cathode or anode for delivery of pacing pulses and/or sensing of cardiac electrical signals, as opposed to delivering high voltage cardioversion defibrillation shocks. In some instances, electrodes 28 and 30 may provide only pacing functionality, only sensing functionality or both.

ICD 14 may obtain cardiac electrical signals corresponding to electrical activity of heart 8 via a combination of sensing vectors that include combinations of electrodes 24, 26, 28 and/or 30. In some examples, housing 15 of ICD 14 is used in combination with one or more of electrodes 24, 26, 28 and/or 30 in a sensing electrode vector. Various sensing electrode vectors utilizing combinations of electrodes 24, 26, 28, and 30 and housing 15 are described below for acquiring first and second cardiac electrical signals using respective first and second sensing electrode vectors that may be selected by sensing circuitry included in ICD 14.

In the example illustrated in FIGS. 1A and 1B, electrode 28 is located proximal to defibrillation electrode 24, and electrode 30 is located between defibrillation electrodes 24 and 26. One, two or more pace/sense electrodes may be carried by lead body 18. For instance, a third pace/sense electrode may be located distal to defibrillation electrode 26 in some examples. Electrodes 28 and 30 are illustrated as ring electrodes; however, electrodes 28 and 30 may comprise any of a number of different types of electrodes, including ring electrodes, short coil electrodes, hemispherical electrodes, directional electrodes, segmented electrodes, or the like. Electrodes 28 and 30 may be positioned at any location along lead body 18 and are not limited to the positions shown. In other examples, lead 16 may include fewer or more pace/sense electrodes and/or defibrillation electrodes than the example shown here.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIG. 1A as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead body 18, and/or other factors.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18 are each electrically coupled with respective defibrillation electrodes 24 and 26 and pace/sense electrodes 28 and 30, which may be separate respective insulated conductors within the lead body 18. The respective conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28 and 30 and transmit sensed electrical signals from one or more of defibrillation electrodes 24 and 26 and/or pace/sense electrodes 28 and 30 to the sensing circuit within ICD 14.

The lead body 18 of lead 16 may be formed from a non-conductive material, including silicone, polyurethane, fluoropolymers, mixtures thereof, and other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zig-zagging.

In the example shown, lead body 18 includes a curving distal portion 25 having two "C" shaped curves, which together may resemble the Greek letter epsilon, "ε." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in pending U.S. Pat. Publication No. 2016/0158567 (Marshall, et al.), incorporated herein by reference in its entirety. The techniques disclosed herein are not limited to any particular lead body design, however. In other examples, lead body 18 is a flexible elongated lead body without any pre-formed shape, bends or curves. Various example configurations of extra-cardiovascular leads and electrodes and dimensions that may be implemented in conjunction with the cardiac event sensing techniques disclosed herein are described in pending U.S. Publication No. 2015/0306375 (Marshall, et al.) and pending U.S. Publication No. 2015/0306410 (Marshall, et al.), both of which are incorporated herein by reference in their entirety.

ICD 14 analyzes the cardiac electrical signals received from one or more sensing electrode vectors to monitor for abnormal rhythms, such as bradycardia, ventricular tachycardia (VT) or ventricular fibrillation (VF). ICD 14 may analyze the heart rate and morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated herein by reference in its entirety.

ICD 14 generates and delivers electrical stimulation therapy in response to detecting a tachyarrhythmia (e.g., VT or VF) using a therapy delivery electrode vector which may be selected from any of the available electrodes 24, 26, 28

30 and/or housing 15. ICD 14 may deliver anti-tachycardia pacing (ATP) in response to VT detection, and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, and 30 and the housing 15 of ICD 14.

FIGS. 1A and 1B are illustrative in nature and should not be considered limiting of the practice of the techniques disclosed herein. ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor 52, memory 53, display 54, user interface 56 and telemetry unit 58. Processor 52 controls external device operations and processes data and signals received from ICD 14. Display 54, which may include a graphical user interface, displays data and other information to a user for reviewing ICD operation and programmed parameters as well as cardiac electrical signals retrieved from ICD 14. For example, as described in conjunction with FIG. 5, a clinician may view cardiac electrical signals received from ICD 14 during a slow, non-paced rhythm for establishing reference P-wave signal amplitudes used by ICD 14 for detecting P-wave oversensing.

User interface 56 may include a mouse, touch screen, key pad or the like to enable a user to interact with external device 40 to initiate a telemetry session with ICD 14 for retrieving data from and/or transmitting data to ICD 14, including programmable parameters for controlling cardiac event sensing and therapy delivery. Telemetry unit 58 includes a transceiver and antenna configured for bidirectional communication with a telemetry circuit included in ICD 14 and is configured to operate in conjunction with processor 52 for sending and receiving data relating to ICD functions via communication link 42.

Communication link 42 may be established between ICD 14 and external device 40 using a radio frequency (RF) link such as BLUETOOTH®, Wi-Fi, or Medical Implant Communication Service (MICS) or other RF or communication frequency bandwidth or communication protocols. Data stored or acquired by ICD 14, including physiological signals or associated data derived therefrom, results of device diagnostics, and histories of detected rhythm episodes and delivered therapies, may be retrieved from ICD 14 by external device 40 following an interrogation command.

External device 40 may be embodied as a programmer used in a hospital, clinic or physician's office to retrieve data from ICD 14 and to program operating parameters and algorithms in ICD 14 for controlling ICD functions. External device 40 may alternatively be embodied as a home monitor or hand held device. External device 40 may be used to program cardiac signal sensing parameters, cardiac rhythm detection parameters and therapy control parameters used by ICD 14. At least some control parameters used in detecting P-wave oversensing according to techniques disclosed herein may be programmed into ICD 14 using external device 40 in some examples.

Figure 2A:
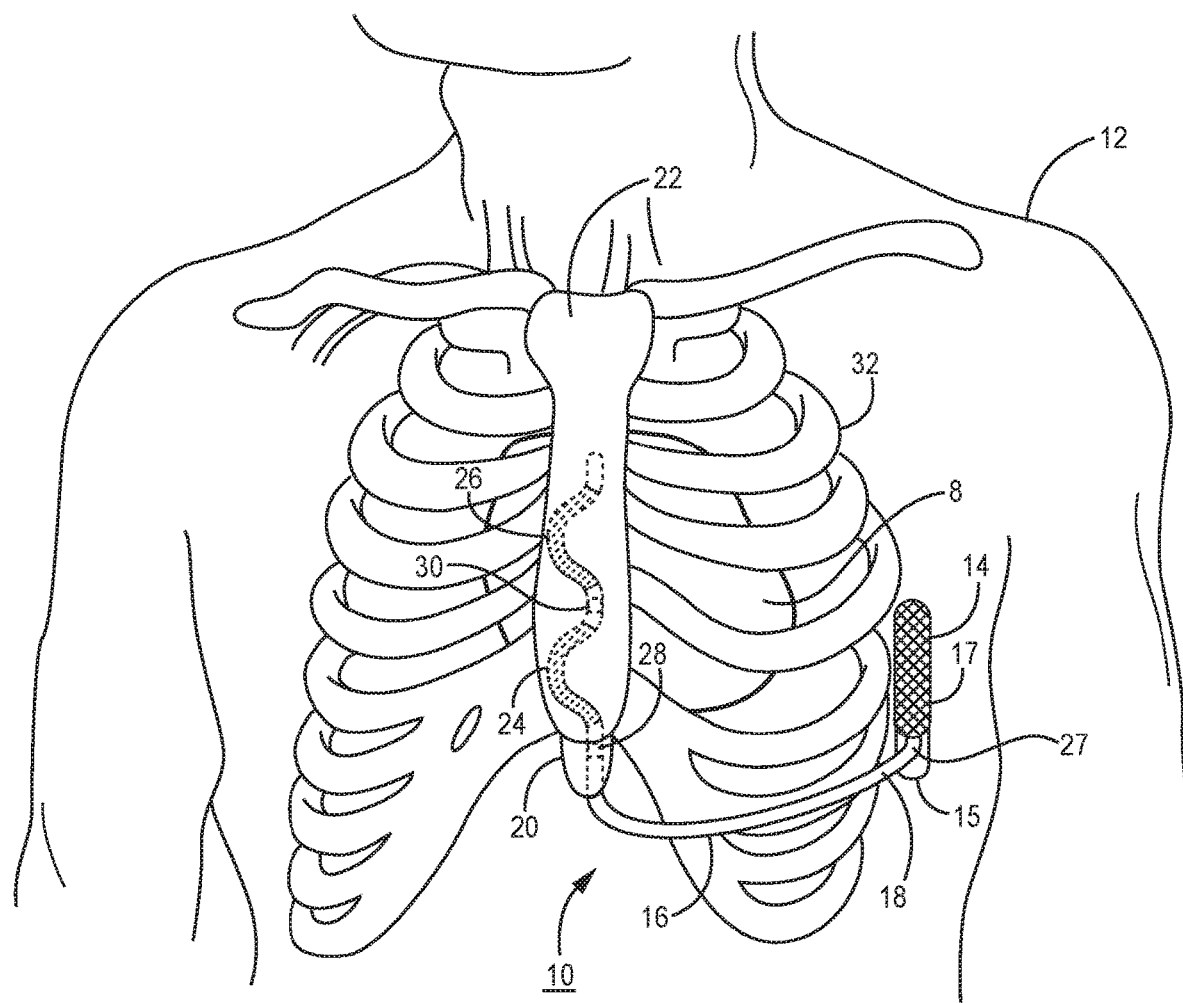
FIGS. 2A-2C are conceptual diagrams of a patient implanted with the extra-cardiovascular ICD system in a different implant configuration than the arrangement shown in FIGS. 1A-1B.
Figure 2B:
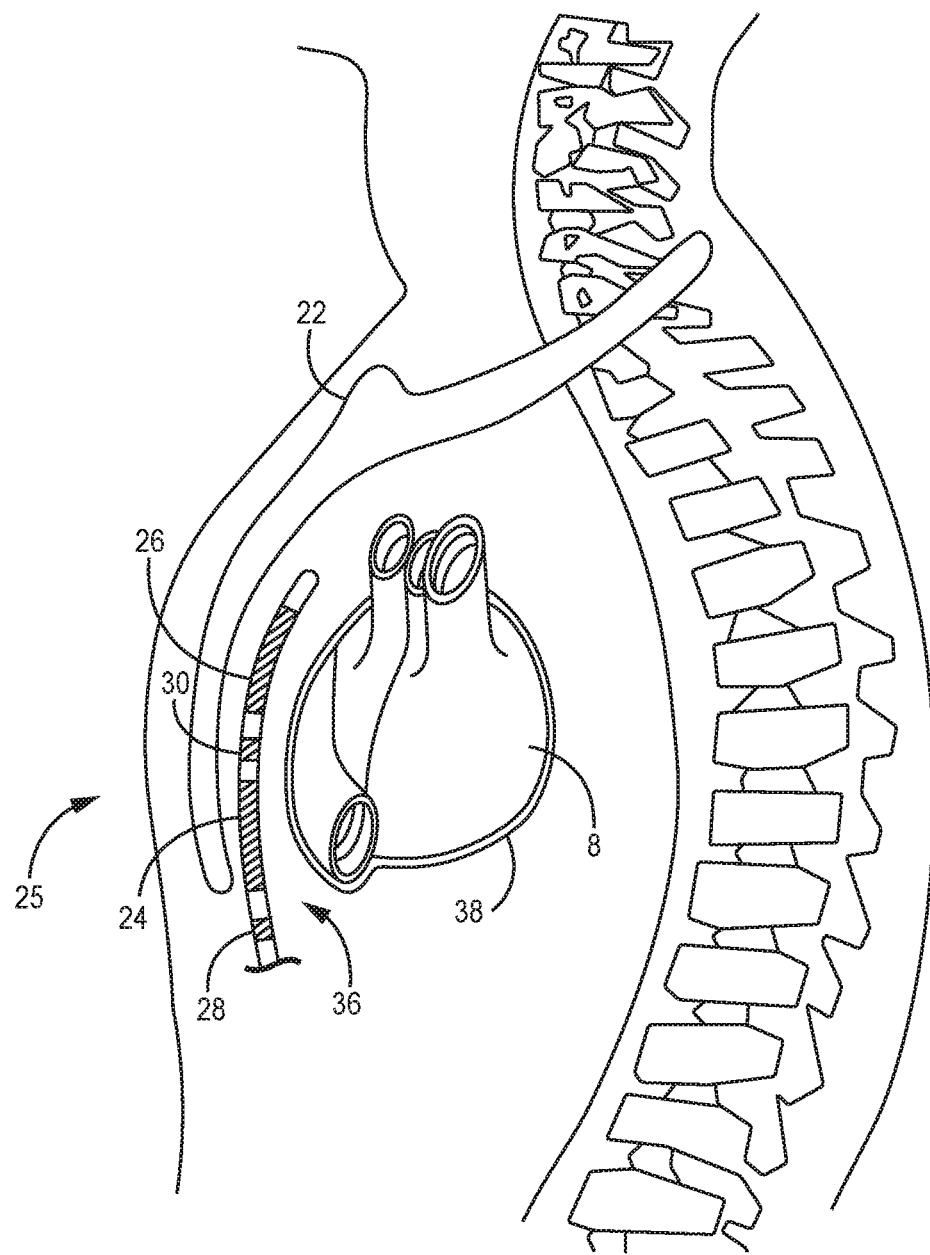
Figure 2C:
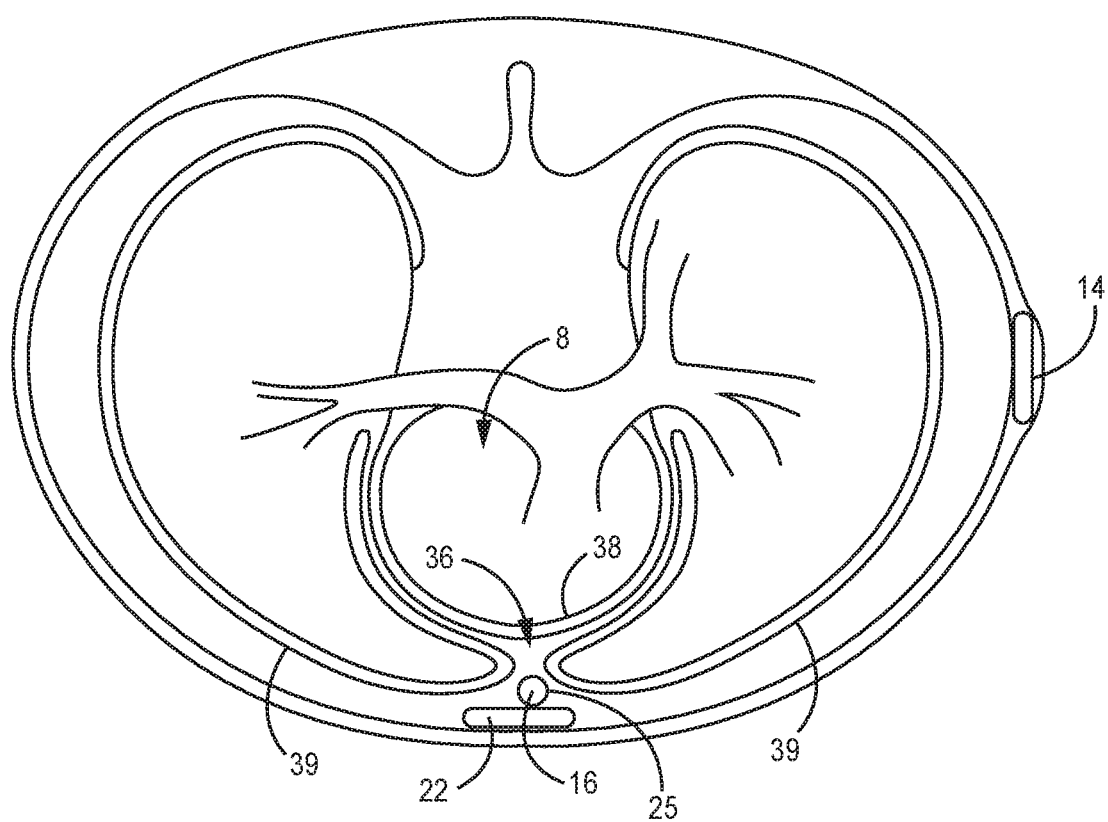

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, extra-cardiovascular lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22 (see FIG. 2C). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to but typically not within the pericardium 38 of heart 8. Other implant locations and lead and electrode arrangements that may be used in conjunction with the cardiac event sensing techniques described herein are generally disclosed in the above-incorporated references.

Figure 3:
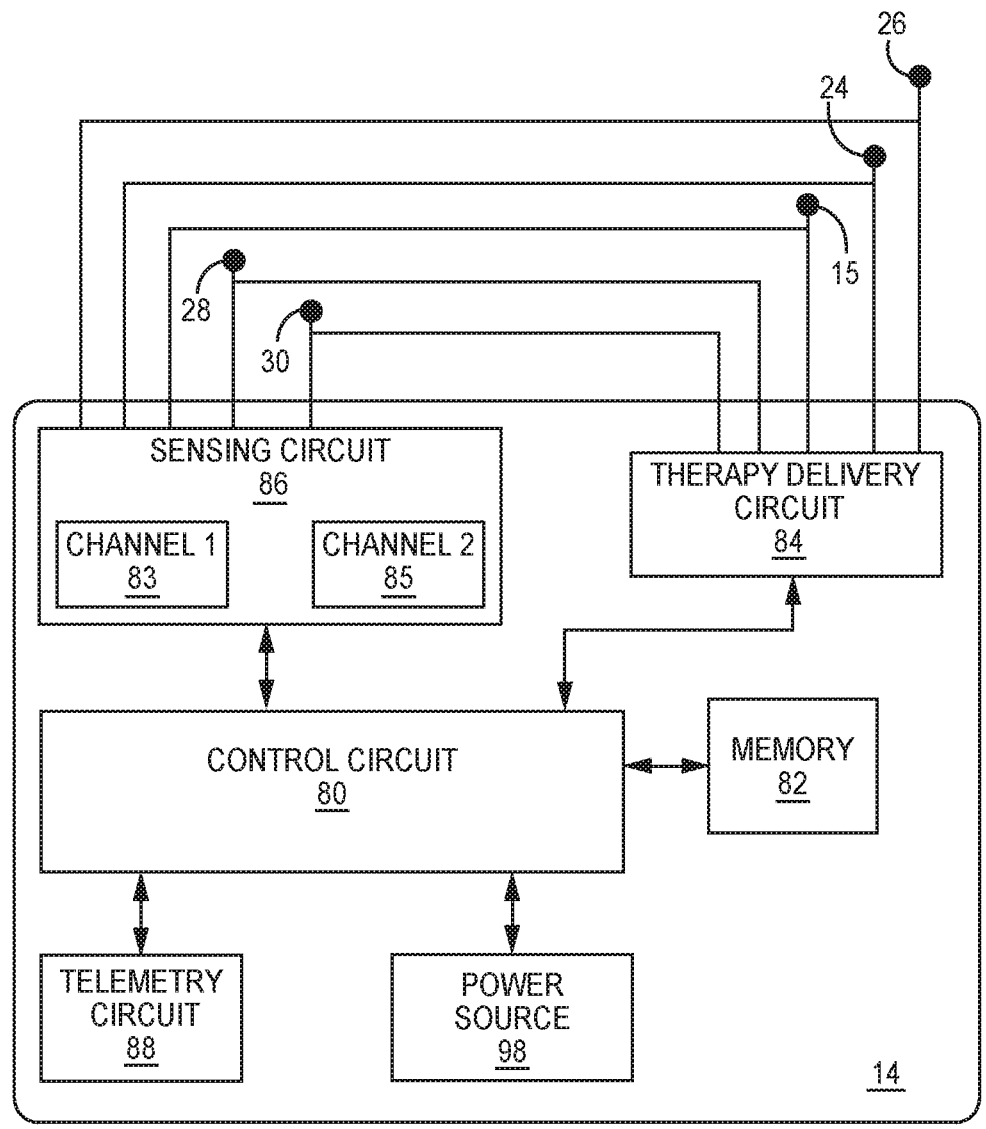
FIG. 3 is a schematic diagram of the ICD of FIGS. 1A-20 according to one example.

FIG. 3 is a schematic diagram of ICD 14 according to one example. The electronic circuitry enclosed within housing 15 (shown schematically as an electrode in FIG. 3) includes software, firmware and hardware that cooperatively monitor cardiac electrical signals, determine when an electrical stimulation therapy is necessary, and deliver therapy as needed according to programmed therapy delivery algorithms and control parameters. ICD 14 is coupled to an extra-cardiovascular lead, such as lead 16 carrying extra-cardiovascular electrodes 24, 26, 28, and 30, for delivering electrical stimulation pulses to the patient's heart and for sensing cardiac electrical signals.

ICD 14 includes a control circuit 80, memory 82, therapy delivery circuit 84, sensing circuit 86, and telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 3, but are not shown for the sake of clarity. For example, power source 98 may be coupled to one or more charging circuits included in therapy delivery circuit 84 for charging holding capacitors included in therapy delivery circuit 84 that are discharged at appropriate times under the control of control circuit 80 for producing electrical pulses according to a therapy protocol, such as for ventricular pacing during atrio-ventricular conduction block or bradycardia, post-shock pacing, ATP and/or CV/DF shock pulses. Power source 98 is also coupled to components of sensing circuit 86, such as sense amplifiers, analog-to-digital converters, switching circuitry, etc. as needed.

The circuits shown in FIG. 3 represent functionality included in ICD 14 and may include any discrete and/or integrated electronic circuit components that implement analog and/or digital circuits capable of producing the functions attributed to ICD 14 herein. Functionality associated with one or more circuits may be performed by separate hardware, firmware or software components, or integrated within common hardware, firmware or software components. For example, cardiac event sensing may be performed cooperatively by sensing circuit 86 and control circuit 80 and may include operations implemented in a processor or other signal processing circuitry included in control circuit 80 executing instructions stored in memory 82 and control signals such as blanking and timing intervals and sensing threshold amplitude signals sent from control circuit 80 to sensing circuit 86. The various circuits of ICD 14 may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in an ICD or pacemaker and by the particular detection and therapy delivery methodologies employed by the ICD or pacemaker. Providing software, hardware, and/or firmware to accomplish the described functionality in the context of any modern implantable cardiac device system, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 carried by lead 16 and the housing 15, which may function as a common or ground electrode or as an active can electrode for delivering CV/DF shock pulses or cardiac pacing pulses.

Sensing circuit 86 may be selectively coupled to electrodes 28, 30 and/or housing 15 in order to monitor electrical activity of the patient's heart. Sensing circuit 86 may additionally be selectively coupled to defibrillation electrodes 24 and/or 26 for use in a sensing electrode vector together or in combination with one or more of electrodes 28, 30 and/or housing 15. Sensing circuit 86 may be enabled to selectively receive cardiac electrical signals from at least two sensing electrode vectors from the available electrodes 24, 26, 28, 30, and housing 15. At least two cardiac electrical signals from two different sensing electrode vectors may be received simultaneously by sensing circuit 86. Sensing circuit 86 may monitor one or both of the cardiac electrical signals simultaneously for sensing cardiac electrical events and producing digitized cardiac signal waveforms for analysis by control circuit 80. For example, sensing circuit 86 may include switching circuitry for selecting which of electrodes 24, 26, 28, 30, and housing 15 are coupled to a first sensing channel 83 and which are coupled to a second sensing channel 85 of sensing circuit 86.

Each sensing channel 83 and 85 may be configured to amplify, filter and digitize the cardiac electrical signal received from selected electrodes coupled to the respective sensing channel to improve the signal quality for detecting cardiac electrical events, such as R-waves or performing other signal analysis. The cardiac event detection circuitry within sensing circuit 86 may include one or more sense amplifiers, filters, rectifiers, threshold detectors, comparators, analog-to-digital converters (ADCs), timers or other analog or digital components as described further in conjunction with FIG. 4. A cardiac event sensing threshold may be automatically adjusted by sensing circuit 86 under the control of control circuit 80, based on timing intervals and sensing threshold values determined by control circuit 80, stored in memory 82, and/or controlled by hardware, firmware and/or software of control circuit 80 and/or sensing circuit 86.

Upon detecting a cardiac electrical event based on a sensing threshold crossing by a received cardiac signal, sensing circuit 86 may produce a sensed event signal, such as an R-wave sensed event signal, that is passed to control circuit 80. The R-wave sensed event signals may be used by control circuit 80 to reset a pacing escape interval used to control the basic timing of pacing pulses generated by therapy delivery circuit 84. R-wave sensed event signals may also be used by control circuit 80 for determining RR intervals (RRIs) for detecting tachyarrhythmia and determining a need for therapy. An RRI is the time interval between two consecutively sensed R-waves and may be determined between two consecutive R-wave sensed event signals received from sensing circuit 86.

Control circuit 80 may include comparators and counters for counting RRIs that fall into various rate detection zones for determining a ventricular rate or performing other rate- or interval-based assessments for detecting VT and VF. For example, control circuit 80 may compare the determined RRIs to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter included in control circuit 80. When a VT or VF interval counter reaches a threshold count value, often referred to as "number of intervals to detect" or "NID," a ventricular tachyarrhythmia may be detected by control circuit 80.

To support additional cardiac signal analyses performed control circuit 80, sensing circuit 86 may pass a digitized cardiac electrical signal to control circuit 80. A cardiac electrical signal from the selected sensing channel, e.g., from first sensing channel 83 and/or the second sensing channel 85, may be passed through a filter and amplifier, provided to a multiplexer and thereafter converted to multi-bit digital signals by an analog-to-digital converter, all included in sensing circuit 86, for storage in memory 82.

Therapy delivery circuit 84 includes charging circuitry, one or more charge storage devices such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Control circuit 80 may include various timers or counters that control when cardiac pacing pulses are delivered. For example, a timing control circuit included in control circuit 80 may include programmable digital counters set by a microprocessor of the control circuit 80 for controlling the basic pacing time intervals associated with various pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

In response to detecting VT or VF, control circuit 80 may control therapy delivery circuit 84 to deliver therapies such as ATP and/or CV/DF therapy. Therapy can be delivered by initiating charging of high voltage capacitors via a charging circuit, both included in therapy delivery circuit 84. Charging is controlled by control circuit 80 which monitors the voltage on the high voltage capacitors, which is passed to control circuit 80 via a charging control line. When the voltage reaches a predetermined value set by control circuit 80, a logic signal is generated on a capacitor full line and passed to therapy delivery circuit 84, terminating charging. A CV/DF pulse is delivered to the heart under the control of the timing circuit 90 by an output circuit of therapy delivery circuit 84 via a control bus. The output circuit may include an output capacitor through which the charged high voltage capacitor is discharged via switching circuitry, e.g., an H-bridge, which determines the electrodes used for delivering the cardioversion or defibrillation pulse and the pulse wave shape.

In some examples, the high voltage therapy circuit configured to deliver CV/DF shock pulses can be controlled by control circuit 80 to deliver pacing pulses, e.g., for delivering ATP, post shock pacing pulses or ventricular pacing pulses during atrio-ventricular conduction block or bradycardia. In other examples, therapy delivery circuit 84 may include a low voltage therapy circuit for generating and delivering pacing pulses for a variety of pacing needs. Therapy delivery and control circuitry generally disclosed in any of the incorporated references may be implemented in ICD 14.

It is recognized that the methods disclosed herein may be implemented in an IMD that is used for monitoring cardiac electrical signals by sensing circuit 86 and control circuit 80 without having therapy delivery capabilities or in an IMD that monitors cardiac electrical signals and delivers cardiac pacing therapies by therapy delivery circuit 84, without high voltage therapy capabilities, such as cardioversion/defibrillation shock capabilities or vice versa.

Control parameters utilized by control circuit 80 for sensing cardiac events and controlling therapy delivery may be programmed into memory 82 via telemetry circuit 88. Telemetry circuit 88 includes a transceiver and antenna for communicating with external device 40 (shown in FIG. 1A) using RF communication or other communication protocols as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12.

Figure 4:
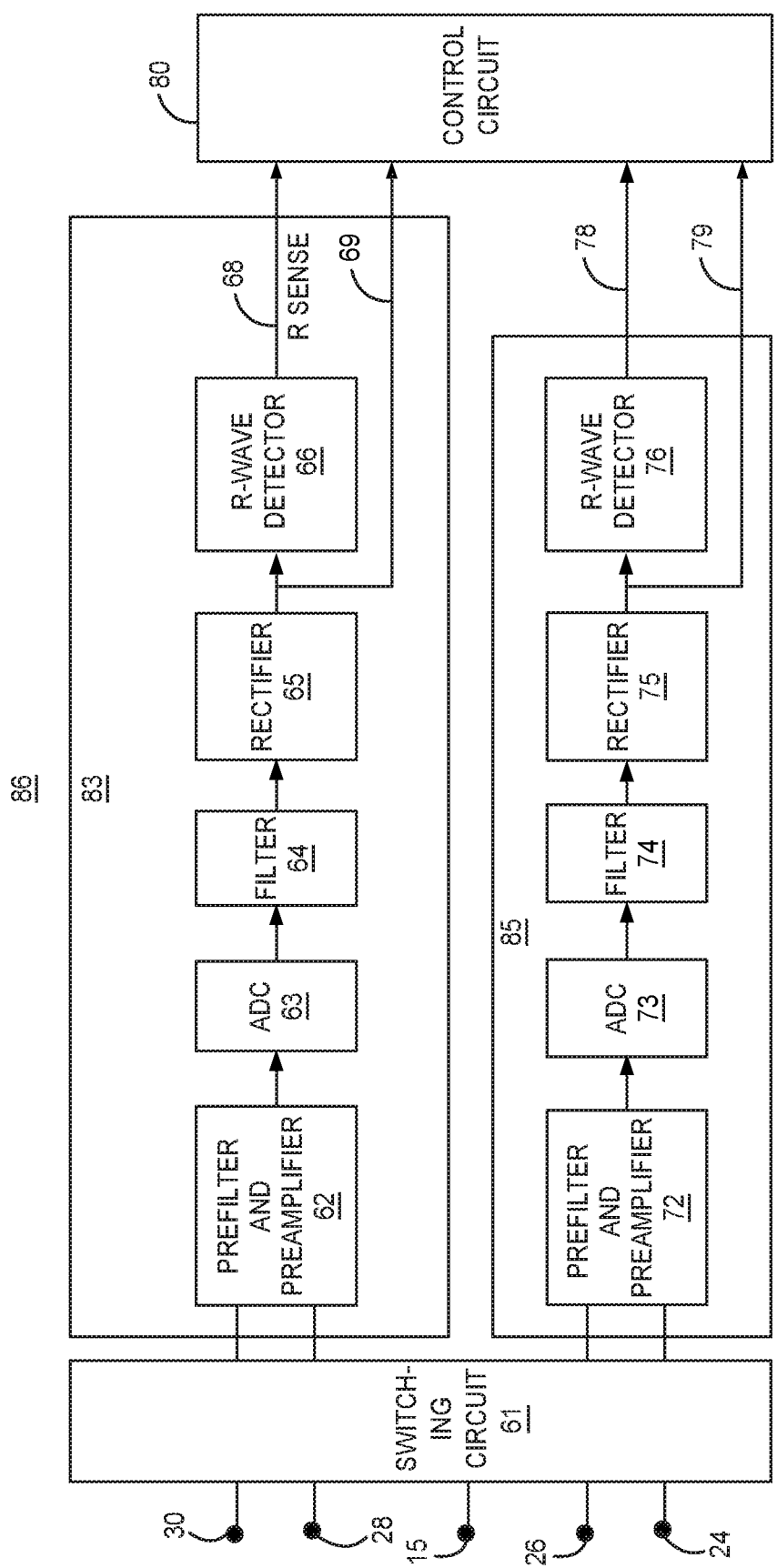
FIG. 4 is a diagram of circuitry included in the sensing circuit of the ICD of FIG. 3 according to one example.

FIG. 4 is a diagram of circuitry included in sensing circuit 86 having first sensing channel 83 and second sensing channel 85 according to one example. Switching circuitry 61 may include a switch array, switch matrix, multiplexer, or any other type of switching device suitable to selectively couple first and second sensing channels 83 and 85 to respective sensing electrode vectors. First sensing channel 83 may be selectively coupled via switching circuitry 61 to a first sensing electrode vector including at least one electrode carried by extra-cardiovascular lead 16 as shown in FIGS. 1A-20 for receiving a first cardiac electrical signal. First sensing channel 83 may be coupled to a sensing electrode vector that is a short bipole, having a relatively shorter inter-electrode distance or spacing than the second electrode vector coupled to second sensing channel 85. First sensing channel 83 may be coupled to a sensing electrode vector that is approximately vertical (when the patient is in an upright position) or approximately aligned with the cardiac axis to increase the likelihood of a relatively high R-wave signal amplitude relative to P-wave signal amplitude. In one example, the first sensing electrode vector may include pace/sense electrodes 28 and 30. In other examples, the first sensing electrode vector coupled to sensing channel 83 may include a defibrillation electrode 24 and/or 26, e.g., a sensing electrode vector between pace/sense electrode 28 and defibrillation electrode 24 or between pace/sense electrode 30 and either of defibrillation electrodes 24 or 26. In still other examples, the first sensing electrode vector may be between defibrillation electrodes 24 and 26.

Sensing circuit 86 includes second sensing channel 85 that receives a second cardiac electrical signal from a second sensing vector, for example from a vector that includes one electrode 24, 26, 28 or 30 carried by lead 16 paired with housing 15. Second sensing channel 85 may be selectively coupled to other sensing electrode vectors, which may form a relatively longer bipole having an inter-electrode distance or spacing that is greater than the sensing electrode vector coupled to first sensing channel 83 in some examples and may be approximately orthogonal to the first channel sensing electrode vector in some cases. For instance, defibrillation electrodes 26 and housing 15 may be coupled to second sensing channel 85 to provide the second cardiac electrical signal. As described below, the second cardiac electrical signal received by second sensing channel 85 via a long bipole may be used by control circuit 80 for comparative analysis of sensed cardiac event peak amplitudes for detecting P-wave oversensing. The long bipole coupled to second sensing channel 85 may provide a far-field signal compared to the relatively shorter bipole coupled to the first sensing channel. In the relatively more far-field signal, the amplitude of P-waves may be relatively higher than in the more near-field signal. In other examples, any vector selected from the available electrodes, e.g., electrodes 24, 26, 28, 30 and/or housing 15, may be included in a sensing electrode vector coupled to second sensing channel 85. The sensing electrode vectors coupled to first sensing channel 83 and second sensing channel 85 are different sensing electrode vectors, which may have no common electrodes or only one common electrode but not both.

In the illustrative example shown in FIG. 4, the electrical signals developed across the first sensing electrode vector, e.g., electrodes 28 and 30, are received by first sensing channel 83 and electrical signals developed across the second sensing electrode vector, e.g., electrodes 26 and housing 15, are received by second sensing channel 85. The cardiac electrical signals are provided as differential input signals to the pre-filter and pre-amplifier 62 or 72, respectively, of first sensing channel 83 and second sensing channel 85. Non-physiological high frequency and DC signals may be filtered by a low pass or bandpass filter included in each of pre-filter and pre-amplifiers 62 and 72, and high voltage signals may be removed by protection diodes included in pre-filter and pre-amplifiers 62 and 72. Pre-filter and pre-amplifiers 62 and 72 may amplify the pre-filtered signal by a gain of between 10 and 100, and in one example a gain of 17.5, and may convert the differential signal to a single-ended output signal passed to analog-to-digital converter (ADC) 63 in first sensing channel 83 and to ADC 73 in second sensing channel 85. Pre-filters and amplifiers 62 and 72 may provide anti-alias filtering and noise reduction prior to digitization.

ADC 63 and ADC 73, respectively, convert the first cardiac electrical signal from an analog signal to a first digital bit stream and the second cardiac electrical signal to a second digital bit stream. In one example, ADC 63 and ADC 73 may be sigma-delta converters (SDC), but other types of ADCs may be used. In some examples, the outputs of ADC 63 and ADC 73 may be provided to decimators (not shown), which function as digital low-pass filters that increase the resolution and reduce the sampling rate of the respective first and second cardiac electrical signals.

The digital outputs of ADC 63 and ADC 73 are each passed to respective filters 64 and 74, which may be digital bandpass filters. The bandpass filters 64 and 74 may have the same or different bandpass frequencies. For example, filter 64 may have a bandpass of approximately 13 Hz to 39 Hz for passing cardiac electrical signals such as R-waves typically occurring in this frequency range. Filter 74 of the second sensing channel 85 may have a bandpass of approximately 2.5 to 100 Hz. In some examples, second sensing channel 85 may further include a notch filter to filter 60 Hz or 50 Hz noise signals.

The bandpass filtered signals are passed from filters 64 and 74 to rectifiers 65 and 75, respectively to produce a filtered, rectified signal. First sensing channel 83 includes an R-wave detector 66 for sensing cardiac events in response to the first cardiac electrical signal crossing an R-wave sensing threshold. The second sensing channel 85 may optionally include an R-wave detector 76 as shown. In other examples, the second sensing channel 85 does not include R-wave detector 76. The filtered, rectified digital cardiac electrical signals 69 and 79 from sensing channel 83 and sensing channel 85 may be passed to control circuit 80 for use in detecting P-wave oversensing as described below in conjunction with FIGS. 5-7. For instance, control circuit 80 is configured to determine a peak amplitude of at least one of the digitized cardiac electrical signals 69 or 79 following an R-wave sensed event signal for use in detecting P-wave oversensing as described below. The digital signals 69 and 79 may also be used by control circuit 80 in detecting and discriminating tachyarrhythmia episodes.

R-wave detector 66 (and 76 if included) may include an auto-adjusting sense amplifier, comparator and/or other detection circuitry that compares the filtered and rectified cardiac electrical signal to an R-wave sensing threshold in real time and produces an R-wave sensed event signal 68 (and/or 78) when the cardiac electrical signal crosses the R-wave sensing threshold outside of a post-sense blanking interval.

The R-wave sensing threshold may be a multi-level sensing threshold as disclosed in pending U.S. patent application Ser. No. 15/142,171 (Cao, et al., filed on Apr. 29, 2016), incorporated herein by reference in its entirety. Briefly, the multi-level sensing threshold may have a starting sensing threshold value held for a time interval, which may be equal to a tachycardia detection interval or expected R-wave to T-wave interval, then drops to a second sensing threshold value held until a drop time interval expires, which may be 1 to 2 seconds long. The sensing threshold drops to a minimum sensing threshold, which may correspond to a programmed sensitivity sometimes referred to as the "sensing floor", after the drop time interval. In other examples, the R-wave sensing threshold used by R-wave detector 66 may be set to a starting value based on the peak amplitude determined during the most recent post-sense blanking interval and decay linearly or exponentially over time until reaching a minimum sensing threshold. The techniques described herein are not limited to a specific behavior of the sensing threshold. Instead, other decaying, step-wise adjusted or other automatically adjusted sensing thresholds may be utilized.

The configuration of sensing channels 83 and 85 shown in FIG. 4 is illustrative in nature and should not be considered limiting of the techniques described herein. The sensing channels 83 and 85 of sensing circuit 86 may include more or fewer components than illustrated and described in FIG. 4.

Figure 5:
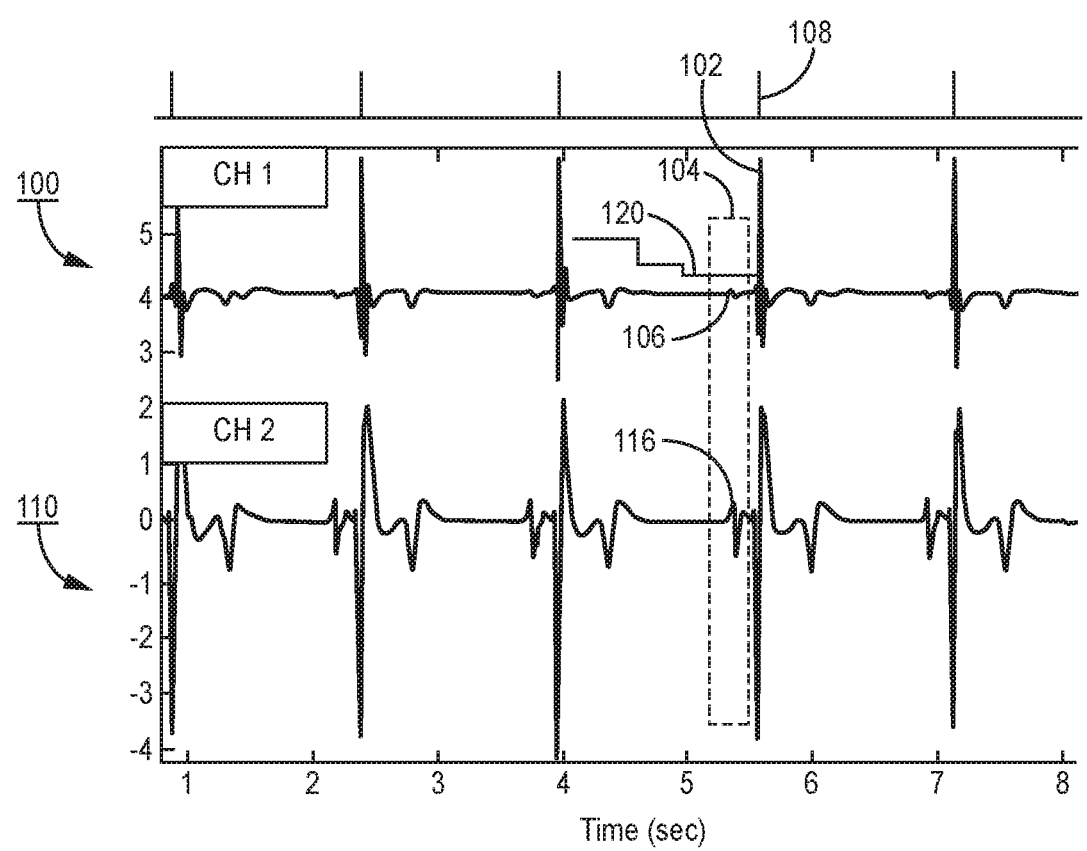
FIG. 5 is a diagram of two cardiac electrical signals provided by the sensing circuit of FIG. 4.

FIG. 5 is a diagram of two cardiac electrical signals 100 and 110 provided by the first sensing channel 83 and second sensing channel 85, respectively, of sensing circuit 86. The signals 100 and 110 are shown prior to rectification by rectifiers 65 and 75. The first sensing channel 83 may sense each R-wave 102 and produce an R-wave sensed event signal 108 in response to cardiac electrical signal 100 crossing an R-wave sensing threshold 120. R-wave sensing threshold 120 is shown as a multi-level threshold which may be automatically adjusted to different sensing threshold values at specified time intervals by sensing circuit 86 under the control of control circuit 80.

Control circuit 80 may be configured to establish a reference peak amplitude of the P-waves 106 and 116 for each sensing channel 83 and 85, respectively. Control circuit 80 may buffer each cardiac electrical signal 100 and 110 over one or more cardiac cycles, e.g., from one R-wave sensed event signal to the next. Control circuit 80 may set a P-wave window 104 at a predetermined time interval earlier than a given R-wave sensed event signal 108. P-wave window 104 may extend up to 300 ms earlier than the R-wave sensed event signal 108. In one example, P-wave window 104 begins 200 ms earlier than the R-wave sensed event signal 108 and is 100 to 150 ms long. In some examples, the P-wave window 104 may be adjusted manually by a clinician interacting with external device 40. For instance, signals 100 and 110 may be transmitted from ICD 14 to external device 40 and displayed on display 54 (FIG. 1A). The clinician may adjust the starting time, ending time and/or width (duration) of P-wave window 104. The timing of the manually adjusted P-wave window may be transmitted to ICD 14 from external device 40 and used for setting P-wave windows relative to R-wave sensed event signals. The starting, ending and duration of P-wave window 104 may be stored in memory 82 for use by control circuit 80 in automatically updating reference P-wave amplitude values during a resting (slow) non-paced heart rhythm.

The P-wave window 104 is applied to both the first cardiac electrical signal 100 and the second cardiac electrical signal 110. The maximum peak amplitude during the P-wave window 104 is determined from the first sensing channel signal 100 and from the second sensing channel signal 110 to obtain a reference peak amplitude for each of the sensing channels 100 and 110, respectively. While non-rectified signals 100 and 110 are shown in FIG. 5, it is to be understood that the peak amplitudes within P-wave window 104 may be determined from the filtered, rectified signal outputs 69 and 79 of the respective sensing channels 83 and 85.

In the example shown, the second cardiac electrical signal 110 has relatively higher amplitude P-waves 116 than the relatively small P-waves 106 of the first cardiac signal 100. This relative difference in P-wave amplitude between the first and second signals 100 and 110 of the respective first and second sensing channels 83 and 85 may be used in detecting P-wave oversensing. When the first sensing channel 83 is coupled to a relatively shorter bipole that is relatively more proximate to the patient's ventricular chambers and/or more aligned with the cardiac axis than the sensing vector coupled to the second cardiac channel 85, the cardiac signal 100 is expected to include relatively higher amplitude R-waves and lower amplitude P-waves. If the second sensing channel 85 is coupled to a relatively long bipole that is less proximate to the ventricular chambers and/or closer to atrial chambers, cardiac signal 110 is expected to have relatively larger P-waves 116 than the first cardiac signal 100. The relative differences between P-wave amplitudes 106 and 116 and/or the reference values of P-wave amplitudes 106 and 116 may be used for detecting P-wave oversensing as described below.

Figure 6:
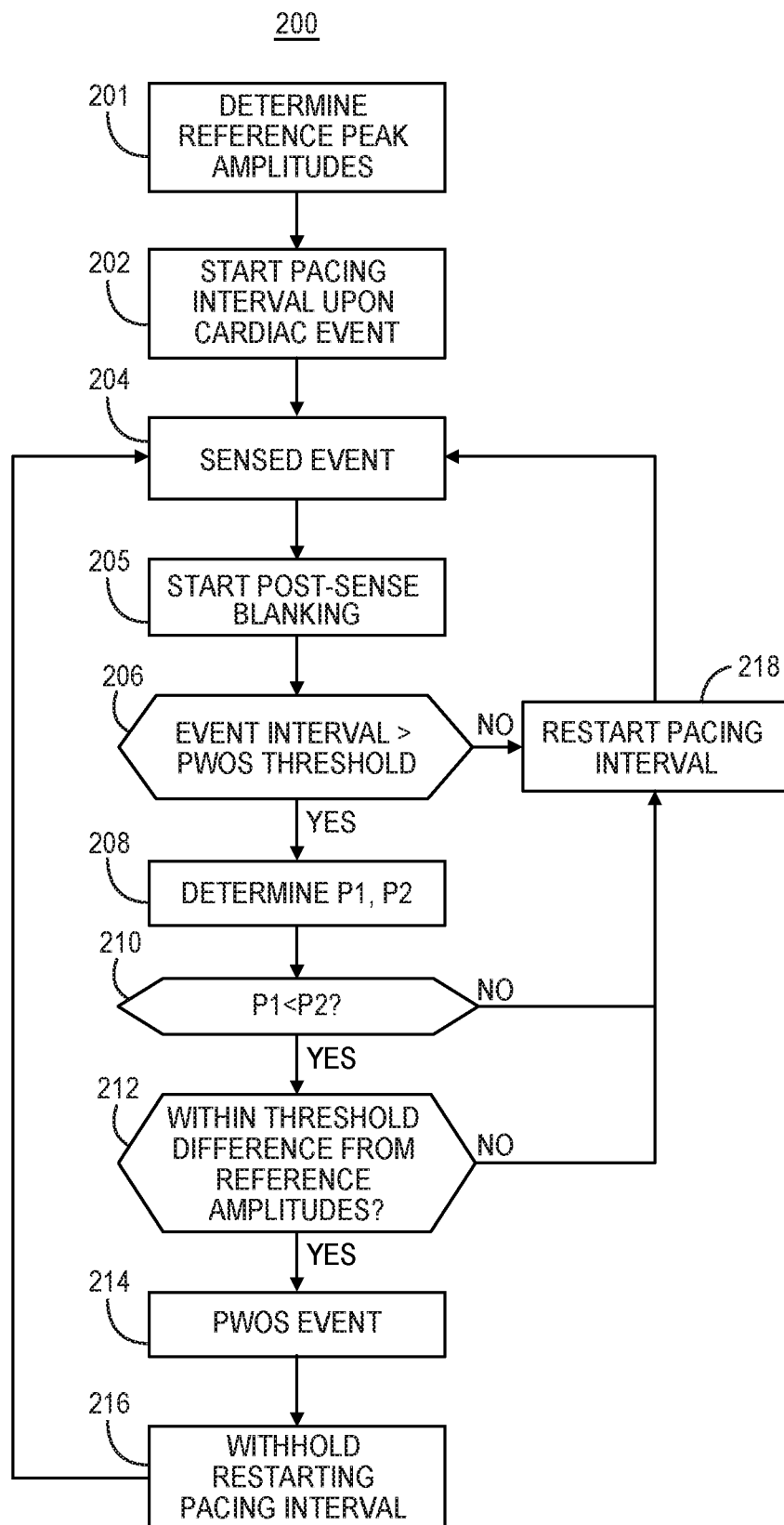
FIG. 6 is a flow chart of a method for detecting P-wave oversensing (PWOS) according to one example.

FIG. 6 is a flow chart 200 of a method performed by ICD 14 for detecting P-wave oversensing (PWOS) according to one example. At block 201, control circuit 80 may determine reference P-wave peak amplitudes from each of the two cardiac electrical signals received by sensing circuit 86. The reference peak amplitudes may be determined during a slow (e.g., resting), intrinsic (non-paced) rhythm as described above in conjunction with FIG. 5.

At block 202, control circuit 80 may start a pacing interval controlled by a timer or counter included in control circuit 80. The pacing interval is started upon a cardiac event, which may be a delivered pacing pulse or an initially sensed intrinsic cardiac event. At block 204, the first sensing channel 83 senses a cardiac event during the pacing interval based on an R-wave sensing threshold crossing by the first cardiac electrical signal. The first sensing channel 83 may produce an R-wave sensed event signal that is passed to control circuit 80. Control circuit 80 starts a post-sense blanking interval at block 205. The post-sense blanking interval may be 100 to 200 ms long, e.g., 150 ms. The post-sense blanking interval avoids double sensing of a single R-wave and oversensing of non-cardiac noise within a physiological refractory period of the myocardium.

Control circuit 80 is configured to detect event intervals that are greater than a P-wave oversensing (PWOS) threshold interval. Control circuit 80 determines the cardiac event interval since the most recent preceding cardiac event (sensed or paced) to the current R-wave sensed event signal at block 206. The cardiac event interval ending with the currently sensed event is compared to the PWOS threshold interval at block 206. In order to detect the currently sensed event as a PWOS event, the cardiac event interval ending with the currently sensed event may be required to be greater than the PWOS threshold interval, e.g., greater than 600 ms. The PWOS threshold interval may be greater than 400 ms in other examples.

The PWOS threshold interval may be set by control circuit 80 to be greater than a tachyarrhythmia detection interval to prevent a low amplitude R-wave during a ventricular tachyarrhythmia from being falsely detected as PWOS, potentially delaying or preventing an appropriate VT or VF detection. During relatively fast rhythms, cardiac pacing to treat asystole or bradycardia is not needed. As such, PWOS detection for controlling pacing timing intervals during fast rhythms, e.g., event intervals shorter than 400 to 600 ms, may not be needed. During a slow rhythm, undetected PWOS may interfere with pacing delivery if a P-wave is falsely sensed as an R-wave, causing a pacing pulse to be inhibited. As such, the requirement of the cardiac event interval being greater than a PWOS threshold interval enables PWOS to be detected when the cardiac event interval is longer than the longest tachyarrhythmia detection interval such that the rate of sensed events is relatively slow and the potential need for cardiac pacing exists. The PWOS threshold interval requirement for detecting PWOS avoids false PWOS detection during fast rhythms which could interfere with tachyarrhythmia detection.

The PWOS threshold interval may be a fixed interval, which may be programmable by a user, or a variable interval that is set by control circuit 80 based on the programmed pacing rate and/or the longest tachyarrhythmia detection interval. The PWOS threshold interval may be greater than the longest tachyarrhythmia detection interval, which may be 400 ms or less, and less than the pacing interval corresponding to the programmed lower pacing rate. If the programmed pacing rate is 40 pulses per minute, the pacing rate interval is 1500 ms. The PWOS threshold interval may be set by control circuit to half of this pacing interval or 750 ms. In other examples, the PWOS threshold interval may be set to 40% to 70% of the pacing interval corresponding to the programmed lower rate (which may typically be 40 to 60 pulses per minute in most patients) but not less than the longest tachyarrhythmia detection interval.

If the cardiac event interval is not greater than the PWOS threshold at block 206, control circuit 80 may restart the pacing interval timer or counter at block 218. A scheduled pacing pulse is inhibited in response to the sensed event. PWOS is not detected.

If a cardiac event interval greater than the PWOS threshold interval is detected at block 206, control circuit 80 determines the peak amplitude of the first cardiac electrical signal at block 208. The peak amplitude is determined from the first sensing channel 83 during the post sense blanking interval (started at block 205). This peak amplitude may be referred to as P1. At block 208, the control circuit 80 may also determine the peak amplitude of the second cardiac electrical signal received from the second sensing channel 85 during the post-sense blanking interval. This peak amplitude may be referred to as P2.

The illustrative examples presented herein utilize the peak amplitudes of the first and second cardiac signals determined during the post-sense blanking interval. It is contemplated that other signal features may be determined, such as a signal width, slope, or area. The signal area may be determined by summing the amplitudes of each sample point of the signal pulse having the maximum peak amplitude during the post-sense blanking interval. In another example, the average signal width may be determined as the signal area divided by the maximum peak amplitude. It is understood that for each signal feature determined during the post-sense blanking interval for use in detecting PWOS, a reference value for the analogous signal feature is previously established by determining the analogous signal feature during P-wave window 104 (FIG. 5) during a normal, slow, non-paced heart rhythm.

Referring again to FIG. 6, the peak amplitudes P1 and P2 determined from the first and second cardiac electrical signals, respectively, may be compared to each other at block 210. If P1 is not less than P2, the sensed event may not be a P-wave. PWOS criteria may be unsatisfied if P1 is greater than P2 in some examples. PWOS is not detected, and control circuit 80 may restart the pacing interval at block 218 in response to the currently sensed event.

If P1 is less than P2, as expected based on the characteristics of P-waves in the first and second cardiac electrical signals as shown in FIG. 5, the sensed event has a higher likelihood of being an oversensed P-wave. At block 212, control circuit 80 may compare the peak amplitudes P1 and P2 to the respective reference P-wave peak amplitudes previously established for the first channel 83 and the second channel 85 at block 202. Control circuit 80 may compare the peak amplitude P1 to its respective reference value by determining the absolute difference between peak amplitude P1 and the reference value determined for the first sensing channel 83. If the absolute difference is less than a threshold percentage of the reference peak amplitude, the currently sensed event may be an oversensed P-wave.

Similarly, the peak amplitude P2 may be compared to its reference peak amplitude value by determining if the absolute difference between P2 and the reference P-wave peak amplitude determined for the second sensing channel 85 is less than a threshold percentage. If both P1 and P2 are within a threshold percentage of their respective reference values, the sensed event is likely an oversensed P-wave given that P1 is less than P2. The threshold percentage may be 100% or less. The P-wave amplitude is not expected to change from its reference value by more than 100%. Sensed events that have a peak amplitude that represents more than a 100% (or other threshold) change in amplitude from the respective reference P-wave peak amplitude may be true R-waves, in which case the pacing interval should be reset so that the scheduled pacing pulse is inhibited.

If the P1 and P2 amplitudes are more than the threshold difference from their respective references amplitudes, the scheduled pacing pulse is inhibited by restarting the pacing interval at block 218. Control circuit 80 returns to block 204 to wait for the next sensed event. If the P1 and P2 amplitudes are both within the threshold difference from the reference P-wave peak amplitudes, "yes" branch of block 212, PWOS is detected at block 214. Control circuit 80 withholds restarting the pacing interval at block 216. The sensed event identified as a PWOS event does not cause the control circuit 80 to inhibit a scheduled pacing pulse. Control circuit 80 allows the pacing interval to continue running and returns to block 204 to wait for the next sensed event.

In this way, PWOS is detected on an event-by-event basis for use in controlling the pacing timing interval on each cardiac cycle to properly inhibit or deliver a pacing pulse as needed. While not shown in FIG. 6, it is to be understood that if the pacing interval expires before an event is sensed at block 204 that is not detected as PWOS, control circuit 80 controls therapy delivery circuit 84 to deliver a pacing pulse. The pacing interval is restarted in response to the delivered pacing pulse. In this way, the heart rate does not fall below the corresponding pacing lower rate even in the presence of PWOS.

According to the flow chart 200 of FIG. 6, PWOS detection criteria includes a requirement of the cardiac event interval ending with the currently sensed event being greater than the PWOS threshold interval, P1 being greater than P2, and P1 and P2 both being within a predetermined threshold difference from their respective reference P-wave peak amplitude values. It is to be understood that in other examples, any combination of these criteria may be used to identify the currently sensed event as a PWOS event. For instance, the cardiac event interval may be required to be greater than a PWOS threshold interval and at least P1 may be required to be within a threshold difference of the reference P-wave peak amplitude determined for the first sensing channel 83. In another example, the cardiac event interval may be required to be greater than the PWOS threshold interval and both P1 and P2 may be required to within a threshold difference of their respective reference P-wave peak amplitude values. The requirement of P1 being less than P2 may be used in some examples, depending on the sensing electrode vectors being used.

Figure 7:
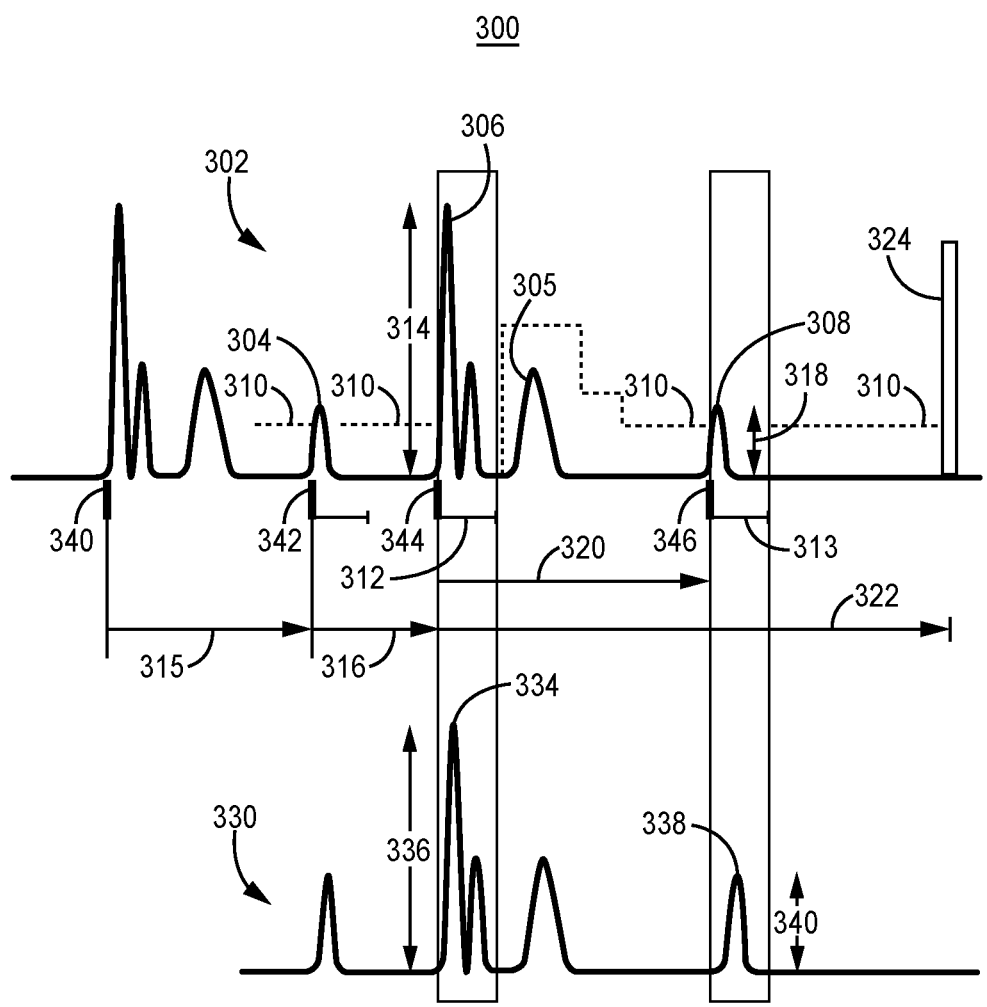
FIG. 7 is a timing diagram depicting an example of PWOS detection and pacing control that may be performed by the ICD of FIG. 3.

FIG. 7 is a timing diagram 300 depicting an example of PWOS detection and pacing control that may be performed by ICD 14. The first cardiac electrical signal 302 is a filtered and rectified signal from the first sensing channel 83. The second cardiac electrical signal 330 is a filtered and rectified signal from the second sensing channel 85. The first sensing channel 83 is configured to control an R-wave sensing threshold 310 and produce R-wave sensed event signals, e.g., signals 340, 342, 344 and 346 in response to the cardiac electrical signal 302 crossing the sensing threshold 310.

In this example, the sensing threshold 310 is shown as a multi-level sensing threshold that is set to a starting value after a post-sense blanking interval 312. The starting value may be based on the peak amplitude of the cardiac signal 302 detected during the post-sense blanking interval 312. The sensing threshold 310 may be adjusted after predetermined time intervals to an intermediate value and finally to a programmed sensitivity or sensing floor. As described above, however, R-wave sensing threshold 310 may be an auto-adjusted threshold controlled according to a variety of control parameters and techniques. Practice of the PWOS detection techniques disclosed herein are not limited to a particular method for controlling or setting the R-wave sensing threshold 310.

In this example, a P-wave 304 of the first cardiac electrical signal 302 may cross sensing threshold 310 resulting in a sensed event signal 342 being produced by the first sensing channel 83. Control circuit 80 determines a cardiac event interval 315 since the most recent preceding cardiac event, which is sensed event signal 340 in this example. The cardiac event interval 315, which may be determined as the value of the pacing interval timer our counter at the time of receiving sensed event signal 342, is compared to the PWOS threshold interval. If this cardiac event interval 315 is less than the PWOS threshold interval, PWOS is not detected, and the sensed event signal 342 may be treated as a valid R-wave for controlling the pacing timing interval.

The pacing interval timer or counter is restarted by control circuit 80 in response to the sensed event signal 342, e.g., as shown by interval 316. Even though the sensed event signal is actually associated with an oversensed P-wave 304, PWOS is not detected when the cardiac event interval 315 is less than the PWOS threshold interval. Since R-wave 306 is sensed after P-wave 304, inhibiting a pacing pulse in response to oversensed P-wave 304 does not result in asystole in this example. By setting a PWOS threshold interval, incorrect detection of true tachyarrhythmia events as PWOS is avoided. A tachyarrhythmia detection algorithm may avoid false detection of tachyarrhythmia due to true PWOS based on other VT/VF detection criteria designed to detect VT or VF with high sensitivity and specificity.

R-wave 306 crosses the R-wave sensing threshold 310 resulting in the next sensed event signal 344 being produced. Control circuit 80 determines the cardiac event interval 316, which is less than the PWOS threshold interval. The sensed event signal 344 is treated as a valid R-wave. The pacing pulse scheduled in response to the preceding sensed event signal 342 is inhibited, and the pacing interval is restarted by control circuit 80 in response to sensed event signal 344, as indicated by starting interval 322.

If the P-wave 304 immediately preceding R-wave 306 had not been sensed and sensed event signal 342 not produced, the cardiac event interval since the most recent preceding event 340 to sensed event signal 344 would be interval 315 plus interval 316, which may be greater than the PWOS threshold interval. This scenario of P-wave 304 not being sensed resulting in a sensed event interval between sensed event signal 340 and sensed event signal 344 may be used to illustrate how P-wave oversensing criteria avoids falsely identifying an R-wave 306 as PWOS. In this scenario of P-wave 304 not being sensed such that the sensed event interval ending on sensed event signal 344 is greater than the PWOS threshold interval, control circuit 80 determines the peak amplitudes from the first and second cardiac electrical signals 302 and 330 during post-sense blanking interval 312. The peak amplitude 314 of R-wave 306 would be determined as P1 in this scenario. P1 is compared to the reference P-wave peak amplitude previously established for the first sensing channel 83. Since the R-waves are generally much larger than the P-waves in the first cardiac signal 302, e.g. 3 to 4 times larger or more, the difference between peak amplitude 314 and the reference P-wave amplitude is not less than a difference threshold, e.g., 100%, as required for detecting PWOS. Since this requirement is not satisfied, PWOS would not be detected based on analysis of the P1 peak during post-sense blanking interval 312. Sensed event signal 344 is properly treated as a sensed R-wave and the pacing interval timer or counter is restarted as indicated by interval 322.

In some examples, additional PWOS criteria may be applied as described in conjunction with FIG. 6. If R-wave sensed event signal 344 is received at a sensed event interval greater than the PWOS threshold interval, the peak amplitude 336 of P-wave 334 of the second cardiac signal 330 may be determined as P2. The difference between P2 336 and the reference P-wave amplitude previously established for the second sensing channel 85 may be compared to a threshold difference. Since R-wave 334 is much larger than P-waves in the second cardiac signal 330, the difference between P2 336 determined during post-sense blanking interval 312 and the reference P-wave amplitude determined for the second sensing channel is likely to be greater than the threshold difference, failing to satisfy the PWOS requirement.

The peak amplitudes 314 and 336 may be compared to each other in some examples. PWOS detection criteria may require that P1 be less than P2. Depending on the sensing electrode vectors being used by the first sensing channel 83 and the second sensing channel 85 for acquiring the raw cardiac signals corresponding to the rectified, filtered signals 302 and 330, R-wave 306 may be expected to be larger than R-wave 336 whereas P-waves 304, 308 in the first signal 302 may be expected to be smaller than the P-waves 338 of the second signal 330. As such, if peak amplitude 314 is not less than peak amplitude 336, PWOS is not detected. In this way, multiple requirements for detecting PWOS may prevent R-wave 306 from being falsely detected as PWOS.

Since the PWOS criteria are not satisfied based on the analysis of peak amplitudes 314 and 336, the pacing timer or counter is appropriately restarted, as indicated by interval 322, in response to the sensed event signal 344 corresponding to a valid R-wave 306. The pacing interval timer or counter is set according to a programmed pacing rate by control circuit 80. For example, the pacing interval timer or counter may be set to expire after 1.0 to 1.5 seconds to provide pacing at a lower rate of 60 to 45 pulses per minute, respectively, in the absence of sensed R-waves.

P-wave 308 of first cardiac electrical signal 330 crosses the R-wave sensing threshold 310 causing the next sensed event signal 346 to be produced to be produced during the pacing interval 322 started in response to sensed event signal 344. The post-sense blanking interval 313 is started in response to sensed event signal 346. The cardiac event interval 320 since the most recent preceding sensed event signal 344 is determined, for example by checking how much time of pacing interval 322 has elapsed based on a value of the pacing interval timer or counter. Cardiac event interval 320 is compared to the PWOS threshold interval. If cardiac event interval 320 is detected as an interval longer than the PWOS threshold interval, control circuit 80 determines P1 for the current sensed event as the peak amplitude 318 from the first cardiac signal 302 during post-sense blanking interval 313. Control circuit 80 determines P2 for the current sensed event signal 346 as the peak amplitude 340 from the second cardiac signal 330 during the post-sense blanking interval 313.

P1 and P2 may each be compared to their respective reference P-wave peak amplitudes previously established for first sensing channel 83 and second sensing channel 85. P1 and P2 may also be compared to each other. If the peak amplitudes 318 and 340 are each within a threshold difference from their respective reference peak amplitudes and peak amplitude 318 is less than peak amplitude 340, the sensed event signal 346 is detected as a PWOS event. Sensed event signal 346 is ignored for the purposes of inhibiting a pacing pulse and restarting the pacing interval 322. Restarting of the pacing interval timer or counter is withheld by control circuit 80 such that the pacing interval 322 continues to run.

As described above, other signal features may be determined instead of or in addition to the peak amplitudes 318 and 340. For instance, the areas of the signal 308 and signal 338 may be determined by summing the sample points during the post-sense blanking interval 313 or a portion thereof. An average signal width may be determined by dividing the area by the respective peak amplitude 318 or 340. Other signal features such a peak slope may be determined during the post-sense blanking interval 313 from each of cardiac signal 310 and cardiac signal 330 for comparison to each other and/or to reference values previously established for the given signal feature.

If R-wave sensing threshold 310 was at the programmed sensitivity or sensing floor when P-wave 308 was sensed, R-wave sensing threshold 310 may remain at the programmed sensitivity of sensing floor in response to sensed event signal 346 being identified as a PWOS event. If R-wave sensing threshold 310 was not yet at the sensing floor, sensing circuit 86 may continue to adjust R-wave sensing threshold 310 according to auto-adjusting threshold control parameters, which may be based on peak amplitude 314 of sensed R-wave 306. The peak amplitude 318 determined during post-sense blanking interval 313 may not be used to adjust the R-wave sensing threshold 310 since sensed event signal 346 is identified as a PWOS event. Pacing interval 322 expires without the occurrence of a sensed event not detected as PWOS. Control circuit 80 controls therapy delivery module 84 to deliver a pacing pulse 324 in response to the pacing interval 322 expiring.

Thus, an IMD system and method for detecting PWOS on a sensed event-by-event basis have been presented in the foregoing description with reference to specific embodiments. In other examples, various methods described herein may include steps performed in a different order or different combination than the illustrative examples shown and described herein. Furthermore, P-wave oversensing may successfully be detected in variations that omit one or more steps presented herein. For example, the IMD may neglect the oversensed P-waves in determining a ventricular rate for detecting ventricular tachyarrhythmias, but not provide any pacing therapy that is responsive to the P-wave oversensing. This may be particularly the case in an extra-cardiovascular system in which leads are be positioned extra-thoracically (outside the ribcage and sternum). It is appreciated that various modifications to the referenced embodiments may be made without departing from the scope of the disclosure and the following claims.

The invention claimed is:

1. An implantable medical device comprising:
a therapy delivery circuit configured to generate cardiac pacing pulses;
a sensing circuit configured to receive a first cardiac signal from a patient's heart via sensing electrodes and sense intrinsic cardiac electrical events from the first cardiac signal; and
a control circuit coupled to the sensing circuit and the therapy delivery circuit and configured to:
start a pacing interval;
detect an event interval that is greater than a P-wave oversensing threshold interval, the event interval extending from an intrinsic cardiac electrical event sensed from the first cardiac signal by the sensing circuit to a most recent preceding cardiac event;
determine a first amplitude of the first cardiac signal in response to detecting the event interval greater than the P-wave oversensing threshold interval;
determine that the first amplitude satisfies P-wave oversensing criteria;
withhold restarting of the pacing interval in response to at least the first amplitude satisfying the P-wave oversensing criteria;
detect the pacing interval expiring; and
control the therapy delivery circuit to generate a pacing pulse in response to the pacing interval expiring.

2. The device of claim 1, wherein
the sensing circuit is configured to receive a second cardiac signal from the patient's heart; and
the control circuit is configured to:
determine a second amplitude of the second cardiac signal in response to detecting the event interval greater than the P-wave oversensing threshold interval; and
determine that the P-wave oversensing criteria are met based on the first amplitude and the second amplitude.

3. The device of claim 2, wherein the control circuit is configured to determine the second amplitude by:
setting a post-sense blanking interval in response to the intrinsic cardiac electrical event sensed by the sensing circuit from the first cardiac signal; and
determining a maximum peak amplitude of the second cardiac signal occurring within the post-sense blanking interval.

4. The device of claim 2, wherein the control circuit is configured to determine that the P-wave oversensing criteria are met by:
establishing a first reference amplitude from the first cardiac signal;
establishing a second reference amplitude from the second cardiac signal;
determining that the first amplitude is within a threshold difference of the first reference amplitude and that the second amplitude is within a threshold difference of the second reference amplitude.

5. The device of claim 2, wherein the control circuit is configured to determine that the P-wave oversensing criteria are met by determining that the first amplitude is less than the second amplitude.

6. The device of claim 2, further comprising a housing enclosing the therapy delivery circuit, the sensing circuit and the control circuit and having a connector block for receiving an extra-cardiovascular lead carrying a first sensing electrode pair for receiving the first cardiac signal, the sensing circuit configured to receive the second cardiac signal via a second sensing electrode pair comprising a sensing electrode carried by the extra-cardiovascular lead and the housing.

7. The device of claim 1, wherein the control circuit is configured to set the P-wave oversensing threshold interval based on the pacing interval.

8. The device of claim 1, wherein the control circuit is configured to set the P-wave oversensing threshold interval greater than a tachyarrhythmia detection interval and less than the pacing interval.

9. The device of claim 1, further comprising a housing enclosing the therapy delivery circuit, the sensing circuit and the control circuit and having a connector block for receiving an extra-cardiovascular lead carrying at least one sensing electrode for receiving the first cardiac signal.

10. The device of claim 1, wherein the control circuit is configured to determine that the P-wave oversensing criteria are met by:
establishing a reference amplitude from the first cardiac signal;
determining that the first amplitude is within a threshold difference of the reference amplitude.

11. A method comprising:
sensing intrinsic cardiac electrical events from a first cardiac signal received by a sensing circuit of an implantable medical device via sensing electrodes from a patient's heart;
starting a pacing interval by a control circuit of the implantable medical device;

detecting by the control circuit an event interval that is greater than a P-wave oversensing threshold interval, the event interval extending from an intrinsic cardiac electrical event sensed from the first cardiac signal by the sensing circuit to a most recent preceding cardiac event;

determining a first amplitude of the first cardiac signal in response to detecting the event interval greater than the P-wave oversensing threshold interval;

determining that the first amplitude satisfies P-wave oversensing criteria;

withholding restarting of the pacing interval in response to at least the first amplitude satisfying the P-wave oversensing criteria;

detecting the pacing interval expiring; and generating a pacing pulse by a therapy delivery circuit of the implantable medical device in response to the pacing interval expiring.

12. The method of claim 11, further comprising:

receiving a second cardiac signal from the patient's heart by the sensing circuit;

determining a second amplitude of the second cardiac signal in response to detecting the event interval greater than the P-wave oversensing threshold interval; and determining that the P-wave oversensing criteria are met based on the first amplitude and the second amplitude.

13. The method of claim 12, wherein determining the second amplitude comprises:

setting a post-sense blanking interval in response to the intrinsic cardiac electrical event sensed from the first cardiac signal; and determining a maximum peak amplitude of the second cardiac signal occurring within the post-sense blanking interval.

14. The method of claim 12, wherein determining that the P-wave oversensing criteria are met comprises:

establishing a first reference amplitude from the first cardiac signal;

establishing a second reference amplitude from the second cardiac signal;

determining that the first amplitude is within a threshold difference of the first reference amplitude and that the second amplitude is within a threshold difference of the second reference amplitude.

15. The method of claim 12, wherein determining that the P-wave oversensing criteria are met comprises determining that the first amplitude is less than the second amplitude.

16. The method of claim 12, further comprising receiving the first cardiac signal via a first sensing electrode pair carried by an extra-cardiovascular lead and receiving the second cardiac signal via a second sensing electrode pair comprising a sensing electrode carried by the extra-cardiovascular lead and a housing that encloses the sensing circuit, the therapy delivery circuit and the control circuit.

17. The method of claim 11, further comprising setting the P-wave oversensing threshold interval based on the pacing interval.

18. The method of claim 11, further comprising setting the P-wave oversensing threshold interval greater than a tachyarrhythmia detection interval and less than the pacing interval.

19. The method of claim 11, further comprising receiving the first cardiac signal via at least one sensing electrode carried by an extra-cardiovascular lead.

20. The method of claim 11, wherein determining that the P-wave oversensing criteria are met comprises:

establishing a reference amplitude from the first cardiac signal;

determining that the first amplitude is within a threshold difference of the reference amplitude.

* * * * *